United States Patent
Puchhammer

(10) Patent No.: US 9,572,688 B2
(45) Date of Patent: Feb. 21, 2017

(54) FINGER AND HAND PROSTHESIS

(75) Inventor: Gregor Puchhammer, Vienna (AT)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 347 days.

(21) Appl. No.: 12/158,176

(22) PCT Filed: Dec. 12, 2006

(86) PCT No.: PCT/DE2006/002174
§ 371 (c)(1),
(2), (4) Date: Jun. 19, 2008

(87) PCT Pub. No.: WO2007/076762
PCT Pub. Date: Jul. 12, 2007

(65) Prior Publication Data
US 2009/0018670 A1    Jan. 15, 2009

(30) Foreign Application Priority Data

Dec. 20, 2005   (DE) .................. 10 2005 061 265

(51) Int. Cl.
| A61F 2/54 | (2006.01) |
| A61F 2/58 | (2006.01) |
| A61F 2/50 | (2006.01) |
| A61F 2/76 | (2006.01) |

(52) U.S. Cl.
CPC ........ *A61F 2/586* (2013.01); *A61F 2002/5001* (2013.01); *A61F 2002/764* (2013.01); *A61F 2002/7635* (2013.01); *A61F 2002/7645* (2013.01); *A61F 2002/7665* (2013.01)

(58) Field of Classification Search
CPC ........ A61F 2/588; A61F 2/4241; A61F 2/586; A61F 2002/5001
USPC ............................................ 623/21.11, 21.15
See application file for complete search history.

(56) References Cited

U.S. PATENT DOCUMENTS

| 1,267,121 | A | * | 5/1918 | Sakowski | ................. | A61F 2/54 |
| | | | | | | 623/59 |
| 1,293,478 | A | * | 2/1919 | Lastawskas | ............... | A61F 2/54 |
| | | | | | | 623/63 |
| 1,319,884 | A | * | 10/1919 | McKay | .................... | A61F 2/586 |
| | | | | | | 623/58 |
| 2,567,066 | A | | 5/1948 | Goldman | | |
| 2,545,452 | A | * | 3/1951 | Fletcher | .................. | A61F 2/586 |
| | | | | | | 623/64 |

(Continued)

FOREIGN PATENT DOCUMENTS

| DE | 368427 | 2/1923 |
| DE | 450871 | 10/1927 |

(Continued)

OTHER PUBLICATIONS

International Search Report for PCT/DE2006/002174, 3 pgs., mailed Apr. 19, 2007.

*Primary Examiner* — Bruce E Snow
*Assistant Examiner* — Melissa Hoban
(74) *Attorney, Agent, or Firm* — Holland & Hart

(57) ABSTRACT

The invention relates to a finger prosthesis comprising a base element, which is formed to receive forces and torques and can be provided with an elastic covering to achieve a natural appearance. Furthermore, the invention relates to a hand prosthesis comprising a chassis and a finger prosthesis arranged on it.

20 Claims, 3 Drawing Sheets

(56) References Cited

U.S. PATENT DOCUMENTS

| | | | |
|---|---|---|---|
| 4,114,464 A * | 9/1978 | Schubert | A61F 2/588 623/64 |
| 4,246,661 A * | 1/1981 | Pinson | A61F 2/583 294/111 |
| 4,291,421 A * | 9/1981 | Massey et al. | 623/63 |
| 4,685,924 A | 8/1987 | Massey | |
| 4,792,338 A * | 12/1988 | Rennerfelt | A61F 2/583 414/4 |
| 5,011,497 A * | 4/1991 | Persson et al. | 623/23.41 |
| 5,062,885 A * | 11/1991 | Matsumoto et al. | 75/255 |
| 6,896,704 B1 | 5/2005 | Higuchi et al. | |
| 7,087,092 B1 * | 8/2006 | Landsberger | 623/57 |
| 8,844,080 B2 * | 9/2014 | Stacy | A47J 43/28 2/163 |
| 2002/0134392 A1 * | 9/2002 | Sorrels | A61B 19/04 128/880 |
| 2002/0152538 A1 * | 10/2002 | McDevitt | A41D 13/087 2/163 |
| 2003/0056274 A1 * | 3/2003 | Sorrels | A61B 19/04 2/21 |
| 2004/0015240 A1 | 1/2004 | Archer et al. | |
| 2004/0018799 A1 * | 1/2004 | Lee | A63H 3/46 446/373 |
| 2005/0021154 A1 | 1/2005 | Brimalm | |
| 2005/0043822 A1 | 2/2005 | Didrick | |
| 2005/0268369 A1 * | 12/2005 | Santiago | B42D 9/04 2/21 |
| 2007/0213831 A1 * | 9/2007 | de Cubber | A61F 2/586 623/21.15 |

FOREIGN PATENT DOCUMENTS

| | | |
|---|---|---|
| DE | 2016295 | 10/1971 |
| EP | 1375087 | 1/2004 |
| FR | 2822404 | 9/2002 |
| JP | 50-027319 | 3/1975 |
| JP | 11-076281 | 3/1999 |
| JP | 2000-325375 | 11/2000 |

* cited by examiner

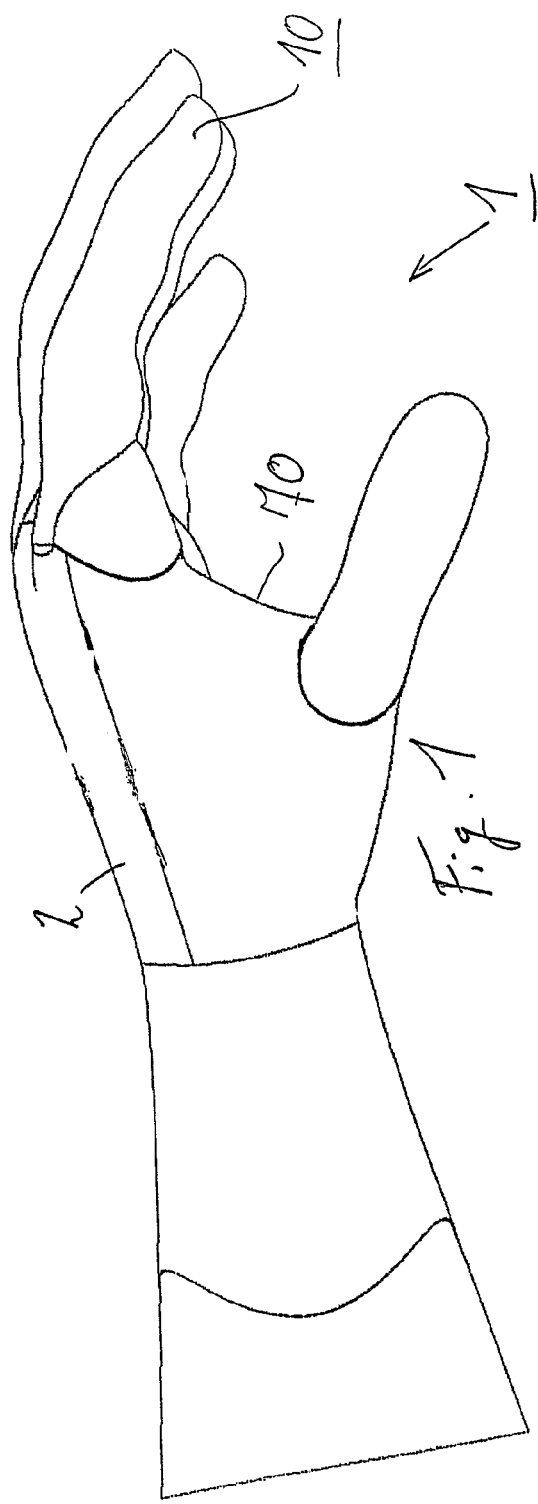

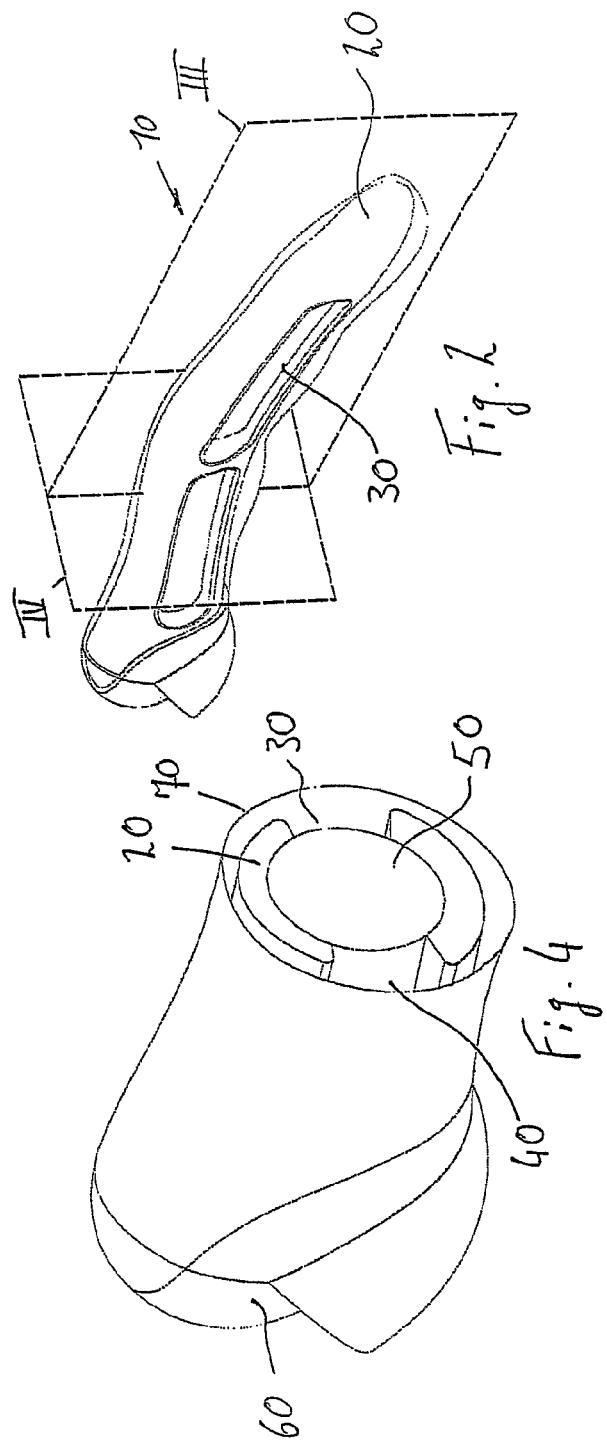

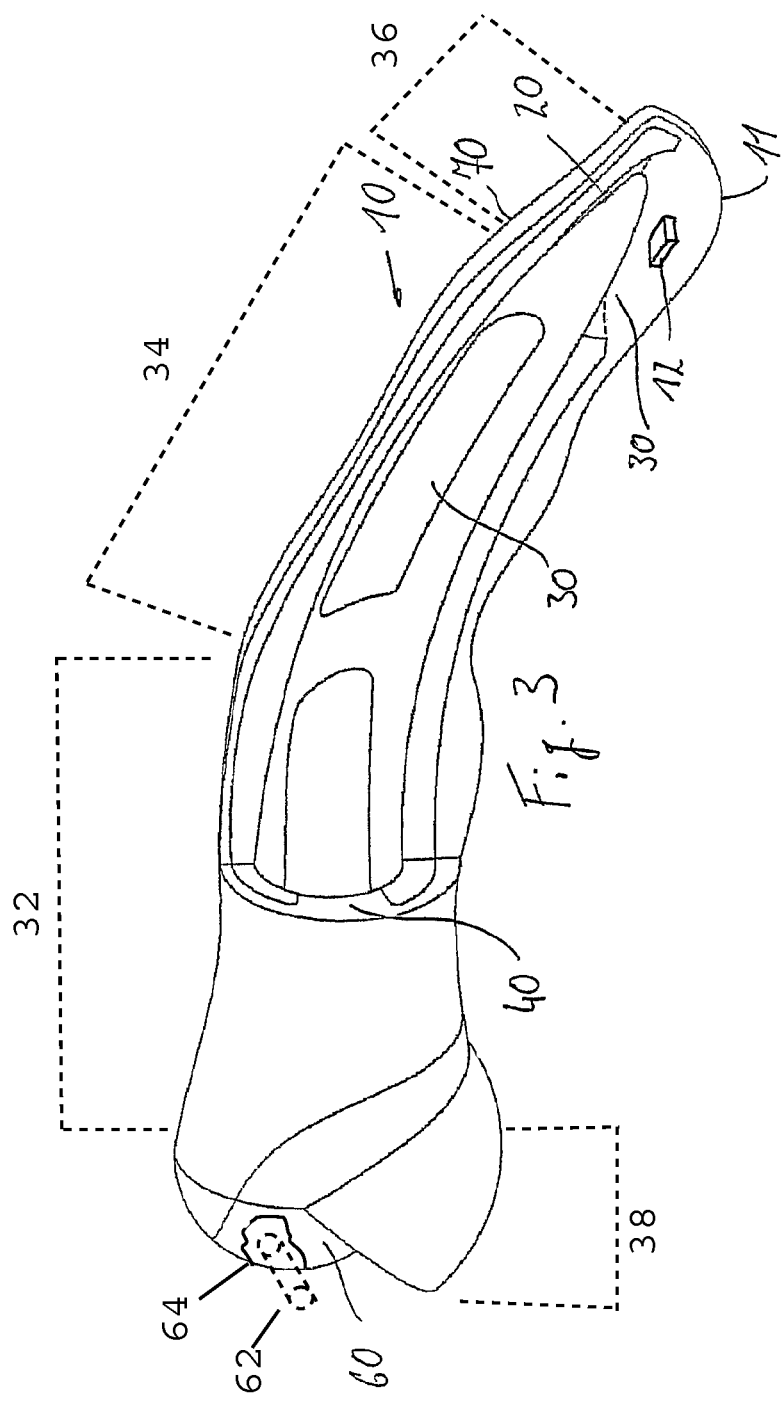

FINGER AND HAND PROSTHESIS

CROSS-REFERENCE TO RELATED APPLICATIONS

This application is a national stage application, filed pursuant to 35 U.S.C. 371, of PCT/DE2006/002174 filed Dec. 12, 2006, which claims priority to DE 10 2005 061 265.2 filed Dec. 20, 2005, both of which are incorporated by reference in their entirety.

FIELD OF THE INVENTION

The invention relates to a finger prosthesis comprising a base element, which is formed to receive forces and torques and can be provided with an elastic covering to achieve a natural appearance. Furthermore, the invention relates to a hand prosthesis comprising a chassis and a finger prosthesis arranged on it.

BACKGROUND

The prior art discloses finger prostheses and hand prostheses with finger prostheses that have a metallic core, which is either formed in one piece or constructed from a number of components that correspond to the phalanxes of the finger and are connected to one another in an articulated manner. The finger prostheses are arranged on a chassis in an articulated manner and can be moved by means of actuators, so that the gripping movement can be replicated. An example of a one-piece construction of a finger prosthesis is described in US 2004/0015240 A1.

Mechanically more complex finger prostheses provide, in addition to the swiveling about the metacarpophalangeal joint, a bending of the finger prosthesis about at least one additional finger joint. Such a configuration is described for example in US 2005/0021154 A1.

To give the finger or hand prosthesis an appearance that looks as natural as possible, a rubber covering in the form of a hand is slipped over the mechanical construction, providing not only a protective function for the mechanical components but also a cushioning and the visual appearance resembling a natural hand. Such a covering is complex to produce, difficult to pull over the mechanical components and corresponds only relatively poorly to the feel of a natural hand.

SUMMARY OF THE INVENTION

An object of the invention is to provide a finger prosthesis and a hand prosthesis that have an improved natural appearance, can be produced at lower cost and can be used easily.

The finger prosthesis according to one embodiment of the invention comprises a base joint, which is formed to receive forces and torques and can include an elastic cover to achieve a natural appearance. The base joint is formed as a dimensionally stable core including clearances that are filled with an elastomer material, which correspond to the soft parts of natural fingers to produce a natural finger contour. Consequently, in addition to the hard base element or core, regions of high elasticity are provided, for example in the region of the fingertips or the surfaces of the phalanxes facing the inner surface of the hand, to provide a feel that is as natural as possible. In the case of motor-driven finger prostheses, improved gripping is thereby made possible since the contact with the gripped objects takes place at elastically deformable regions as in the case of a natural hand, resulting not only increased gripping reliability but also a more natural gripping movement.

In another embodiment of the invention the base element is formed as a hollow body to provide a lightweight overall finger construction. The base element may be made of a polymer, such as a thermoplastic or a composite material, to reduce the weight of the finger prosthesis without restrictions in terms of stability. Alternatively, the base element may be formed from a metal material, such as a lightweight metal or a metal alloy. A combination of plastic and metal may also be used.

In a further embodiment, the base element and the elastomer material are processed together in a two-component injection-molding process, so that the finger prosthesis achieves a final contour or form at the same time as the functional properties of the finger prosthesis arranged on the prosthesis. By producing it in an appropriate color, it is possible to make the finger prosthesis resemble a natural finger with places that are soft on a natural finger being formed as correspondingly soft regions on the finger prosthesis. This makes the process of producing finger prostheses simpler and less costly.

In yet another embodiment, the base element has a broken structure so that the elastomer material extends through the base element. The base element is completely embedded in the elastomer material, at least in certain regions, to provide a high degree of elasticity and a great deformation displacement when an appropriate elastomer material is chosen.

Channels or receiving regions for cables or sensors may be formed in the base element and alternatively or additionally in the elastomer material, for example, to achieve feedback on the position of individual phalanxes in relation to one another and, as a result, the degree of bending of the fingers.

A mounting for an axial spindle of a joint may be formed on the base element, which fastens to a chassis of a prosthesis, it being possible for this mounting to be elastically formed. The mounting may allow a displacement perpendicular to the axis of rotation to achieve an appearance resembling the natural mobility of the fingers. By such "soft" mounting of the finger prosthesis, it is possible for the finger prosthesis to have a lateral displaceability and an additionally yielding nature, e.g., a rigid rotating spindle located in a soft holder or soft mounting. This reduces the impression of a rigid, unnatural, technical mechanism and achieves a natural-looking gripping appearance. To be able to absorb the very high loads on the finger prosthesis and the mounting, which may be up to 50 Nm, metal inserts may be arranged in the region of the metacarpophalangeal joint to reinforce the mounting.

To make it possible to obtain feedback on the gripping force applied, a sensor may be arranged in the region of the fingertip, in particular molded, pressed or adhesively bonded into the elastomer material. The sensor may be formed as a gripping-force, temperature, slip or acceleration sensor.

To achieve further resemblance to a natural finger, an exchangeable plastic covering, designed in the form of skin made to match a natural finger in color and structure, may be arranged over the base element and the elastomer material. This plastic covering may be very thin, such that can be produced at very low cost. The plastic covering can be pulled very easily over the finger prosthesis or the entire hand prosthesis and may cover the regions that are connected to one another in an articulated manner. In the event of damage or irreversible soiling of the plastic covering, it can also be easily changed by the wearer of the prosthesis, like a glove.

The hand prosthesis according to a particular embodiment is provided with a chassis and at least one finger prosthesis such as that which has been described above. With preference, the finger prosthesis is articulated and/or elastically coupled to the chassis, in order to achieve a natural looking appearance by means of a soft mounting.

An exemplary embodiment of the invention is explained in more detail below on the basis of the accompanying figures, in which:

FIG. 1 shows a hand prosthesis;

FIG. 2 shows a finger prosthesis in a partial sectional view;

FIG. 3 shows a finger prosthesis in a partial sectional view according to sectional plane III from FIG. 2; and FIG. 4 shows a finger prosthesis in a cross-sectional view according to sectional plane IV of FIG. 2.

FIG. 1 shows a hand prosthesis 1 comprising a hand chassis 2 and finger prostheses 10 articulated to it. A plastic covering 70 designed to look like skin and made of an elastic material in the form of a glove is pulled over the entire hand prosthesis 1. At least three fingers, namely the thumb, the index finger and the middle finger, are articulated to the chassis 2 in such a way that they can be driven, since many of the everyday gripping tasks can be performed with these three fingers.

FIG. 2 shows the construction of a finger prosthesis 10 comprising a base element 20 with a monolithically formed core, which has a basic contour of a natural finger. The base element 20 is made of a dimensionally stable material, in particular a polymer or composite material, and has clearances 30 in regions that correspond to the phalanxes of the fingers and the fingertip. These clearances 30 are arranged at places corresponding to areas of soft tissue on natural fingers. The structure of the base element 20 is formed in this case in such a way that the clearances 30 do not impair the mechanical stability, so that the forces acting on the finger prosthesis 10 can continue to be reliably absorbed and transmitted. In the present case, the clearances 30 are formed perpendicularly to a plane of movement of the finger prosthesis 10.

FIG. 3 shows the construction of the finger prosthesis 10 in a partial sectional representation. The base element 20 in this case extends substantially over the entire length of the finger, the clearances 30 being formed as apertures through which an elastomer material 40 can pass, so that in certain regions the base element 20 formed as a hollow body can be penetrated by the elastomer material 40. In the region of the fingertip 11, a relatively great clearance or a relatively large region is filled with the elastomer material 40, in a way corresponding to the construction of a natural finger. Embedded in the fingertip is a gripping-force sensor 12, to give feedback to the control unit for controlling the gripping forces to be applied. Alternatively or in addition to a gripping-force sensor 12, a temperature sensor, an acceleration sensor or a slip sensor, which determines a relative movement between the finger prosthesis and a gripped object, may be arranged. This slip sensor may operate optically. The arrangement of the sensors are not restricted to the fingertip but can be fastened at any suitable location in the finger prosthesis.

Arranged in the finger prosthesis 10 in a metacarpophalangeal joint region 38 corresponding to the metacarpophalangeal joint is a soft mounting 60 and a rigid spindle 62 to make lateral displaceability perpendicular to the axis of rotation possible about the metacarpophalangeal joint. Such displaceability reduces the stress on the components and the mounting under loads that may occur for example when the prosthesis knocks against a solid object. To be able to absorb the very high loads on the finger prosthesis and the mounting, which may be up to 50 Nm, one or more metal inserts 64 may be arranged in the metacarpophalangeal joint region 38 to reinforce the mounting 60 and spindle 62. Apart from a rigid and one-piece configuration of the finger prosthesis 10, it is possible to provide it with at least one further joint in addition to the metacarpophalangeal joint.

It can be seen in FIG. 4, in a cross-sectional representation, that the base element 20 is formed as a hollow body, the wall of which is provided with clearances 30 in the form of apertures which are filled with the elastomer material 40. A channel 50, which can receive drives, cables or sensors, may be formed within the base element 20. Alternatively, the hollow space may be filled with the elastomer material 40, as represented in FIG. 3 in the region of the fingertip. The base element 20 is advantageously processed together with the elastomer material 40 in a two-component injection-molding process, so that the contour of the finger prosthesis is complete once the injection-molding operation has ended. It is possible to dispense with the laborious production of a contour-forming plastic covering.

An elastic plastic covering, which may be formed with very thin walls, may be pulled both over an individual finger prosthesis 10 and over the entire hand prosthesis 1, in order to make it possible to provide the finger prosthesis 10 with the texture of skin and a natural color.

The finger prosthesis 10 according to the invention makes the prosthesis hard and soft places corresponding to a natural finger. At the same time the finger prosthesis 10 can be produced very easily, with low weight and, by virtue of the elastomer material 40 being molded to the force-transmitting structure of the base element 20, it works, feels and looks like a natural finger. If not all the finger prostheses 10 on a hand prosthesis 1 are driven, the non-driven fingers may be formed completely from an elastomer, since they generally do not have to transmit any forces.

The invention claimed is:

1. A finger prosthesis comprising:
   a base element having a monolithically formed core, the base element extending substantially over an entire length of the finger prosthesis, the base element being configured to receive forces and torques and including a dimensionally stable material having a metacarpophalangeal joint region, a proximal phalanx region, a middle phalanx region and a fingertip region, the dimensionally stable material further having a hollow body construction with an open channel along its length and clearances at least at the proximal and middle phalanx regions corresponding to soft parts of a natural finger, wherein the clearances are filled with an elastomer material to produce a natural finger contour; and
   an elastic covering positioned over the base element to achieve a natural finger appearance.

2. The finger prosthesis as claimed in claim 1, wherein the base element is made of a polymer or metal.

3. The finger prosthesis as claimed in claim 1, wherein the clearances being formed as apertures.

4. The finger prosthesis as claimed in claim 1, wherein the channels to receive cables or sensors are formed in at least one of the base element and the elastomer material.

5. The finger prosthesis as claimed in claim 1, wherein the base element includes a mounting and an axial spindle at the metacarpophalangeal joint region.

6. The finger prosthesis as claimed in claim 5, wherein the mounting comprises an elastomer material.

7. The finger prosthesis as claimed in claim 5, wherein the mounting further comprises one or more metal inserts to reinforce the mounting.

8. The finger prosthesis as claimed in claim 1, wherein a sensor is arranged in the finger prosthesis.

9. The finger prosthesis as claimed in claim 1, wherein the elastic covering comprises an exchangeable plastic covering in the form of skin, which is arranged over the base element and the elastomer material.

10. The finger prosthesis as claimed in claim 1, wherein the elastomer material encloses at least certain regions of an outer side of the base element.

11. The finger prosthesis of claim 1 formed by a method comprising injection molding the base element and the elastomer material together in a two-component injection-molding process.

12. The finger prosthesis of claim 1 wherein the clearances comprise openings through the base element, the openings extending lengthwise along each of the proximal phalanx portion and middle phalanx portion.

13. A hand prosthesis, comprising:
a chassis;
at least one finger prosthesis, comprising:
    a base element having a monolithically formed core, the base element extending substantially over an entire length of the finger prosthesis, the base element being configured to receive forces and torques and including a dimensionally stable material having a metacarpophalangeal joint region, a proximal phalanx region, a middle phalanx region and a fingertip region, the dimensionally stable material further having a hollow body construction with an open channel along its length and having clearances at least at the proximal and middle phalanx regions corresponding to soft parts of a natural finger, wherein the clearances are filled with an elastomer material to produce a natural finger contour; and
    an elastic covering positioned over the base element to achieve a natural finger appearance.

14. The hand prosthesis as claimed in claim 13, wherein the at least one finger prosthesis is at least one of articulated and elastically coupled to the chassis.

15. The hand prosthesis as claimed in claim 13, wherein an exchangeable plastic covering designed in the form of skin is arranged over the chassis and the finger prosthesis.

16. A finger prosthesis, comprising:
a base element having a monolithically formed core, the base element extending substantially over an entire length of the finger prosthesis, the base element being configured to receive forces and torques, the base element comprising:
    a dimensionally stable material;
    a metacarpophalangeal joint region, a proximal phalanx region, a middle phalanx region and a fingertip region;
    a hollow body construction having an open channel along its length and having clearances at least at the proximal and middle phalanx regions corresponding to soft parts of a natural finger;
an elastomer material positioned in the clearances to provide a natural finger contour;
an elastic covering positioned over the base element to achieve a natural finger appearance.

17. The finger prosthesis as claimed in claim 16, wherein the base element is made of a polymer or metal.

18. The finger prosthesis as claimed in claim 16, wherein the clearances being formed as apertures.

19. The finger prosthesis as claimed in claim 16, wherein the channels to receive cables or sensors are formed in at least one of the base element and the elastomer material.

20. The finger prosthesis as claimed in claim 16, wherein the base element includes a mounting and an axial spindle at the metacarpophalangeal joint region.

* * * * *